(12) United States Patent  
Kanamori et al.

(10) Patent No.: US 12,122,058 B2  
(45) Date of Patent: Oct. 22, 2024

(54) BEAUTY INSTRUMENT AND ELECTRIC RAZOR

(71) Applicant: Panasonic Intellectual Property Management Co., Ltd., Osaka (JP)

(72) Inventors: Yoshiaki Kanamori, Kyoto (JP); Kenji Narita, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 246 days.

(21) Appl. No.: 17/796,191

(22) PCT Filed: Nov. 19, 2020

(86) PCT No.: PCT/JP2020/043173  
§ 371 (c)(1),  
(2) Date: Jul. 28, 2022

(87) PCT Pub. No.: WO2021/157159  
PCT Pub. Date: Aug. 12, 2021

(65) Prior Publication Data  
US 2023/0071286 A1 Mar. 9, 2023

(30) Foreign Application Priority Data

Feb. 4, 2020 (JP) ................. 2020-017022

(51) Int. Cl.  
B26B 19/48 (2006.01)  
A61N 1/04 (2006.01)  
(Continued)

(52) U.S. Cl.  
CPC ............ B26B 19/48 (2013.01); A61N 1/0428 (2013.01); A61N 1/0476 (2013.01); A61N 1/328 (2013.01); A61N 1/3603 (2017.08)

(58) Field of Classification Search  
CPC .... B26B 19/48; A61N 1/3603; A61N 1/0428; A61N 1/0476; A61N 1/328  
(Continued)

(56) References Cited  
U.S. PATENT DOCUMENTS 4,531,287 A * 7/1985 Shibata ................... B26B 19/28  
200/600  
10,537,736 B2 * 1/2020 Hyun ...................... A61B 5/443  
(Continued)

FOREIGN PATENT DOCUMENTS

CN 101541374 A 9/2009  
CN 103566465 A 2/2014  
(Continued)

OTHER PUBLICATIONS

International Search Report issued on Jan. 26, 2021 in International Application No. PCT/JP2020/043173, with English translation.  
(Continued)

Primary Examiner — Omar Flores Sanchez  
(74) Attorney, Agent, or Firm — Rimon P.C.

(57) ABSTRACT

A beauty instrument according to the present disclosure comprises a skin electrode disposed in a head, a grip electrode disposed in a grip, a voltage application circuit for applying a voltage between the skin electrode and the grip electrode to cause a current to flow between the skin electrode and the grip electrode through a human body, and a controller that controls the voltage application circuit. The controller comprises a touch detector that detects touch of a skin surface of the human body with the skin electrode. Before the touch detector detects the touch, the voltage application circuit is controlled to apply a first voltage having a relatively high frequency, and after the touch  
(Continued)

detector detects the touch, the voltage application circuit is controlled to apply a second voltage having a relatively low frequency.

10 Claims, 6 Drawing Sheets

(51) Int. Cl.
*A61N 1/32* (2006.01)
*A61N 1/36* (2006.01)

(58) Field of Classification Search
USPC .......................................................... 30/34.05
See application file for complete search history.

(56) References Cited

U.S. PATENT DOCUMENTS

| | | | | |
|---|---|---|---|---|
| 11,324,948 | B2* | 5/2022 | Jurna | .................... A61B 18/14 |
| 2004/0098066 | A1* | 5/2004 | Pitzen | .................... A61N 1/328 |
| | | | | 607/50 |
| 2010/0076367 | A1 | 3/2010 | Ackermans et al. | |
| 2012/0253246 | A1* | 10/2012 | Yamazaki | .............. A61H 39/04 |
| | | | | 601/101 |
| 2013/0289679 | A1 | 10/2013 | Eckhouse et al. | |
| 2017/0189227 | A1* | 7/2017 | Brunson | ................. A61N 1/325 |
| 2017/0189670 | A1* | 7/2017 | Brunson | ................. A61H 7/001 |
| 2023/0074850 | A1* | 3/2023 | Kanamori | ............... B26B 21/48 |

FOREIGN PATENT DOCUMENTS

| | | |
|---|---|---|
| JP | 56-001155 A | 1/1981 |
| JP | 6-269505 A | 9/1994 |
| JP | 10-295834 A | 11/1998 |
| JP | 2000-316990 A | 11/2000 |
| JP | 2010-510821 A | 4/2010 |
| JP | 2012-152328 A | 8/2012 |
| JP | 2013-534167 A | 9/2013 |
| JP | 2014-033950 A | 2/2014 |
| JP | 2017-070673 A | 4/2017 |
| JP | 2018-015435 A | 2/2018 |

OTHER PUBLICATIONS

English Translation of Chinese Search Report dated Jun. 6, 2024 for the related Chinese Patent Application No. 202080094894.9.

* cited by examiner

BEAUTY INSTRUMENT AND ELECTRIC RAZOR

CROSS-REFERENCE OF RELATED APPLICATIONS

This application is the U.S. National Phase under 35 U.S.C. § 371 of International Patent Application No. PCT/JP2020/043173, filed on Nov. 19, 2020, which in turn claims the benefit of Japanese Patent Application No. 2020-017022, filed on Feb. 4, 2020, the entire disclosures of which Applications are incorporated by reference herein.

TECHNICAL FIELD

The present disclosure relates to a beauty instrument and an electric razor which is an example of the beauty instrument.

BACKGROUND ART

An ion introduction device for enhanced transport of substances through a region of a skin and having an electrode system and an associated controller in order to generate two transport electric fields directed in different directions in the region is described in PTL 1.

Such an ion introduction device is also used in a beauty instrument and an electric razor.

CITATION LIST

Patent Literature

PTL 1: Unexamined Japanese Patent Publication No. 2010-510821

SUMMARY OF THE INVENTION

In the prior art, since an electrical condition between two electrodes (two transport electric fields) at the time of treatment or cutting of hair is constant, an inrush current (a large current that temporarily flows) flows to a skin surface when the electrode touches the skin surface of a user, and the user may feel pain at this time.

The present disclosure has been made in view of such problems of the prior art. An object of the present disclosure is to provide a beauty instrument and an electric razor that can prevent a user from feeling pain when an electrode touches a skin surface of the user during treatment or cutting of hair.

A beauty instrument according to an aspect of the present disclosure comprises a head, a grip, a skin electrode disposed at a position of the head touching a skin surface of a human body, and a grip electrode disposed at a position of the grip touching a finger of the human body. The beauty instrument comprises a voltage application circuit for applying a voltage between the skin electrode and the grip electrode to cause a current to flow between the skin electrode and the grip electrode through the human body, and a controller that controls the voltage application circuit. The controller comprises a touch detector that detects touch of the skin surface of the human body with the skin electrode. The controller controls the voltage application circuit to apply a first voltage when the touch detector does not detect the touch. The controller controls the voltage application circuit to apply a second voltage having a frequency lower than a frequency of the first voltage when the touch detector detects the touch.

An electric razor according to another aspect of the present disclosure comprises a head, a grip, and a blade unit that is disposed in the head for cutting hair. The electric razor comprises a skin electrode that is disposed at a position of the head touching a skin surface of a human body during cutting of hair, and a grip electrode that is disposed at a position of the grip touching a finger of the human body during the cutting of hair. The electric razor further comprises a voltage application circuit for applying a voltage between the skin electrode and the grip electrode to cause a current to flow between the skin electrode and the grip electrode through the human body, and a controller that controls the voltage application circuit. The controller comprises a touch detector that detects touch of the skin surface of the human body with the skin electrode. The controller controls the voltage application circuit to apply a first voltage when the touch detector does not detect the touch. The controller controls the voltage application circuit to apply a second voltage having a frequency lower than a frequency of the first voltage when the touch detector detects the touch.

According to the present disclosure, it is possible to provide the beauty instrument and the electric razor that can prevent the user from feeling pain when the electrode touches the skin surface of the user during treatment or cutting of hair.

DESCRIPTION OF EMBODIMENT

Hereinafter, an exemplary embodiment will be described in detail with reference to the drawings. However, unnecessarily detailed description is omitted in some cases. For example, a detailed description of already well-known matters or a redundant description of substantially the same configuration may be omitted.

Note that, the accompanying drawings and the following description are only presented to help those skilled in the art fully understand the present disclosure, and are not intended to limit the subject matters as claimed in the claims.

Hereinafter, an electric razor for removing hair (shaving) and simultaneously caring a skin surface will be exemplified as a beauty instrument. Note that, the present disclosure is applicable to a facial treatment device, a face massage device, and the like in addition to the electric razor.

Hereinafter, a width direction of the electric razor in front view is referred to as left-right direction X, a depth direction of the electric razor in front view is referred to as front-back direction Y, and a height direction of the electric razor in front view is referred to as up-down direction Z.

Hereinafter, electric razor 10 according to the present exemplary embodiment will be described with reference to FIGS. 1 to 8.

[1. Configuration]

Figure 1:
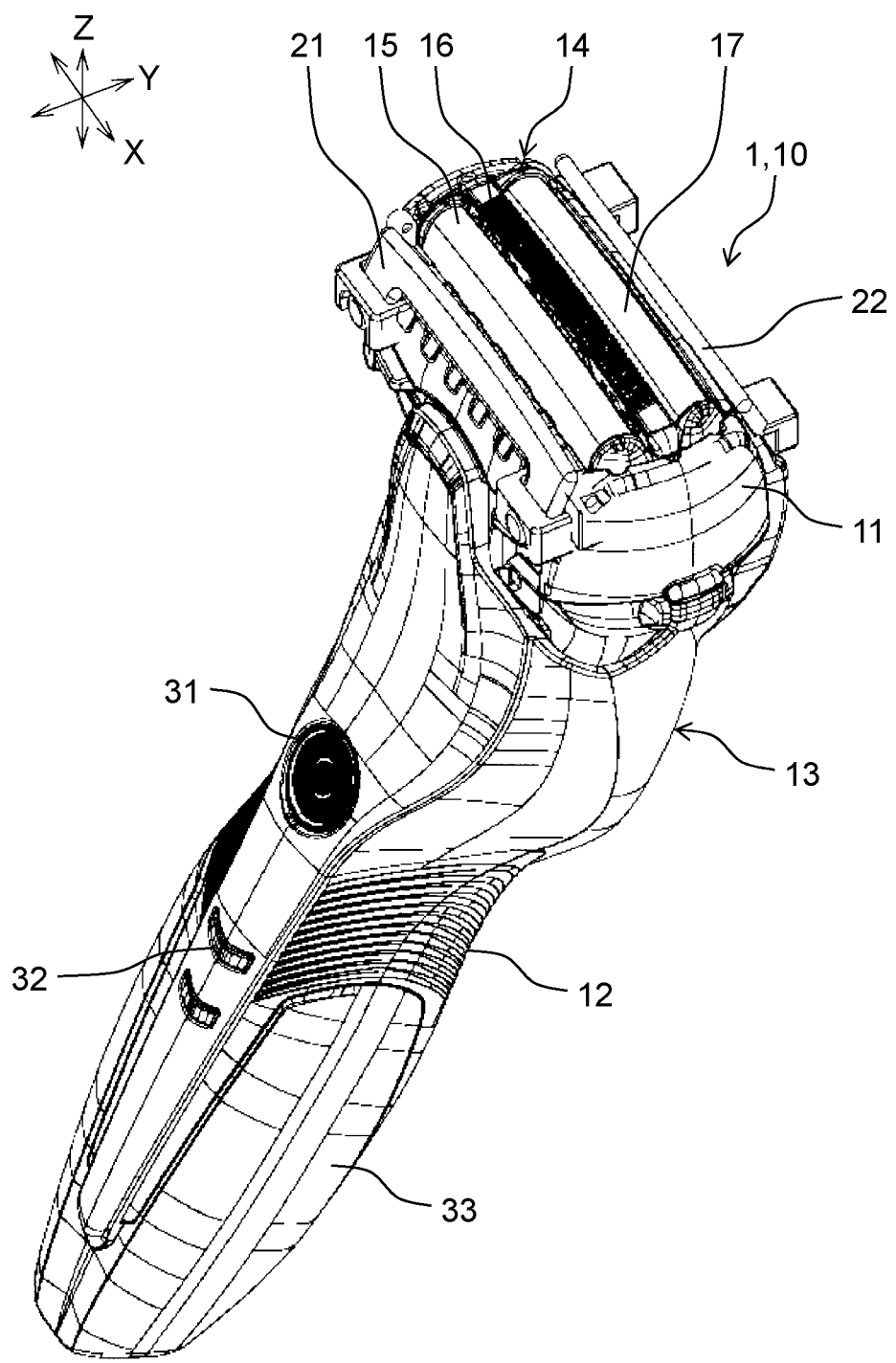
FIG. 1 is a perspective view illustrating an electric razor according to an exemplary embodiment.
Figure 2:
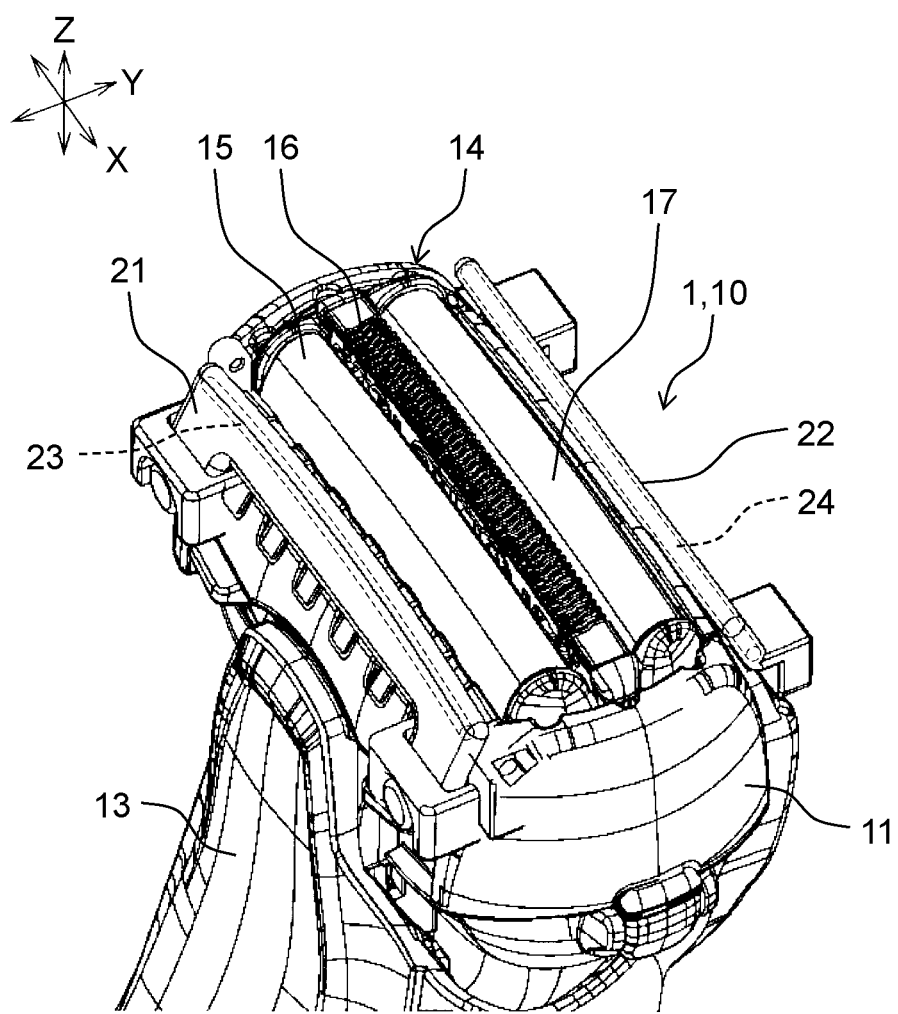
FIG. 2 is an enlarged perspective view illustrating a main part of the electric razor according to the exemplary embodiment.

As illustrated in FIGS. 1 and 2, electric razor 10 according to the present exemplary embodiment includes head 11 and electric razor body 13 having grip 12.

Blade unit 14 for cutting hair such as beard and hair is disposed and held in head 11. Blade unit 14 includes outer net blade (first outer net blade) 15, outer slit blade 16, and outer net blade (second outer net blade) 17. In the present exemplary embodiment, first outer net blade 15, outer slit blade 16, and second outer net blade 17 are disposed in head 11 in this order from a near side in front-back direction Y.

Skin electrode (first skin electrode) 21 for applying a current to a skin surface of a user and skin electrode (second skin electrode) 22 different from first skin electrode 21 are disposed in head 11. First skin electrode 21 and second skin electrode 22 are disposed at positions of head 11 touching the skin surface of the user during shaving.

First skin electrode 21 and second skin electrode 22 are made of a conductor disposed in head 11. An electrical insulation treatment is performed on a surface of the conductor of second skin electrode 22 in order to perform energization of electroporation (electric punch method), which will be described later.

Heater (first heater) 23 is incorporated in first skin electrode 21, and heater (second heater) 24 different from first heater 23 is incorporated in second skin electrode 22. Driving of first heater 23 and second heater 24 is controlled by controller 36, which will be described later.

In the present exemplary embodiment, first skin electrode 21 and second skin electrode 22 are disposed in head 11 in this order from the near side in front-back direction Y, and first skin electrode 21 and second skin electrode 22 are disposed at an interval in front-back direction Y.

Contrary to the present exemplary embodiment, second skin electrode 22 and first skin electrode 21 may be disposed in head 11 in this order from the near side in front-back direction Y.

Blade unit 14 (first outer net blade 15, outer slit blade 16, and second outer net blade 17) is disposed between first skin electrode 21 and second skin electrode 22. That is, first skin electrode 21 and second skin electrode 22 are disposed at an interval equal to or longer than a dimension in front-back direction Y of blade unit 14 with respect to front-back direction Y.

Note that, although not illustrated, a suspension mechanism may be interposed between the skin electrodes (first skin electrode 21 and second skin electrode 22) and head 11. That is, skin electrodes 21 and 22 may include a suspension mechanism interposed between skin electrodes 21 and 22 and head 11. For example, partial touch between skin electrodes 21 and 22 and the skin surface of the user is suppressed by the suspension mechanisms by interposing the suspension mechanism between skin electrodes 21 and 22 and head 11, and skin electrodes 21 and 22 can stably touch the skin surface.

Although not illustrated, a pop-up mechanism may be interposed between the skin electrodes (first skin electrode 21 and second skin electrode 22) and head 11. That is, skin electrodes 21 and 22 may have the pop-up mechanism interposed between skin electrodes 21 and 22 and head 11. As a result, for example, skin electrodes 21 and 22 can be popped up upward in up-down direction Z by the pop-up mechanism, and blade unit 14 can cause skin electrodes 21 and 22 to touch the skin surface of the user without touching the skin surface.

Figure 9:
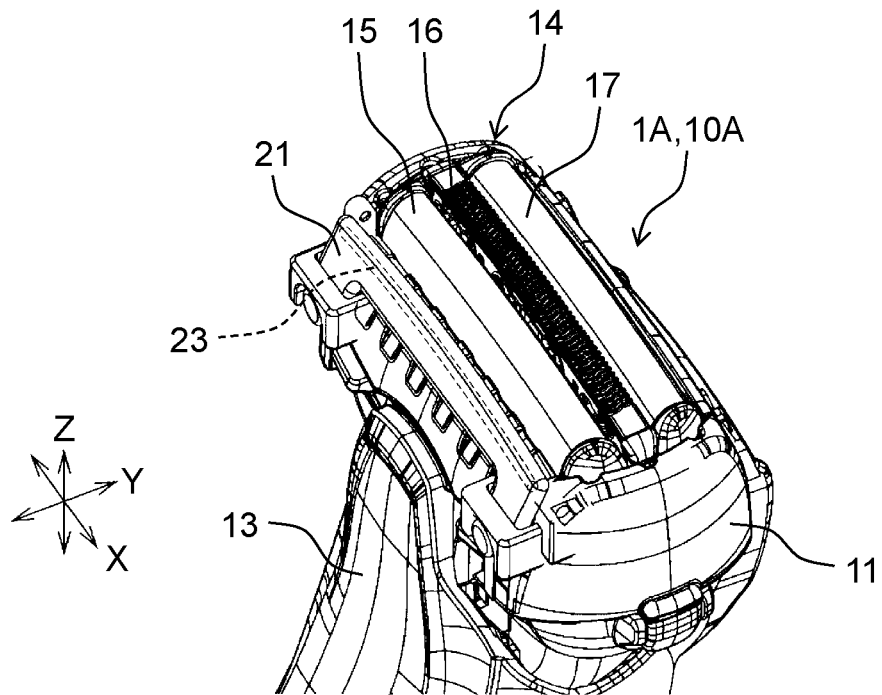
FIG. 9 is an enlarged perspective view of a main part of an electric razor illustrating a skin electrode according to a modification example.

As in electric razor 10A (beauty instrument 1A) illustrated in FIG. 9, only skin electrode (first skin electrode) 21 for applying a current to the skin surface of the user may be disposed in head 11. In FIG. 9, first skin electrode 21 is disposed on the near side in front-back direction Y with respect to blade unit 14. However, for example, first skin electrode 21 may be disposed in blade unit 14, or may be disposed behind blade unit 14 in front-back direction Y. In some cases, a plurality of first skin electrodes 21 may be disposed in head 11 at intervals in left-right direction X.

Figure 10:
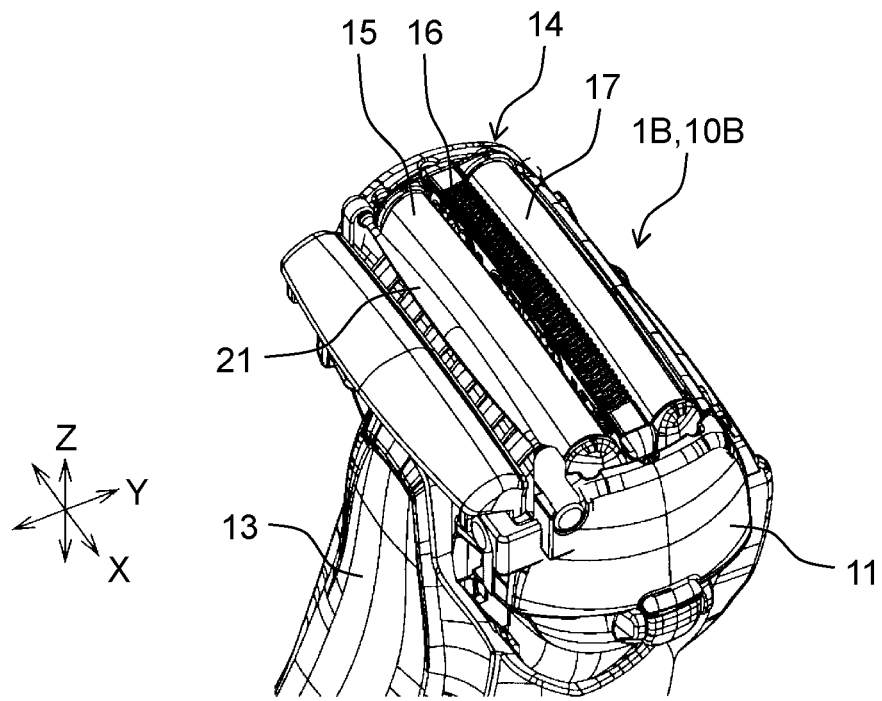
FIG. 10 is an enlarged perspective view of a main part of an electric razor illustrating a skin electrode according to another modification example.

As in electric razor 10B (beauty instrument 1B) illustrated in FIG. 10, roller-shaped skin electrode (first skin electrode) 21 may be disposed in head 11. That is, first skin electrode 21 may be formed in a roller shape in order to function as a beauty treatment roller. In FIG. 10, roller-shaped first skin electrode 21 is disposed on the near side in front-back direction Y with respect to blade unit 14. However, for example, first skin electrode 21 may be disposed in blade unit 14, or may be disposed behind blade unit 14 in front-back direction Y.

As illustrated in FIG. 1, power switch 31 for operating electric razor 10, and changeover switch 32 for switching between skin care modes, which will be described later, are provided in electric razor body 13.

Electric razor body 13 doubles as grip 12 of electric razor 10, and grip electrode 33 is disposed in grip 12. Grip electrode 33 is disposed at a position of grip 12 where the grip electrode touches a finger of the user during shaving.

Grip electrode 33 is made of a conductor disposed on a surface of grip 12.

Figure 3:
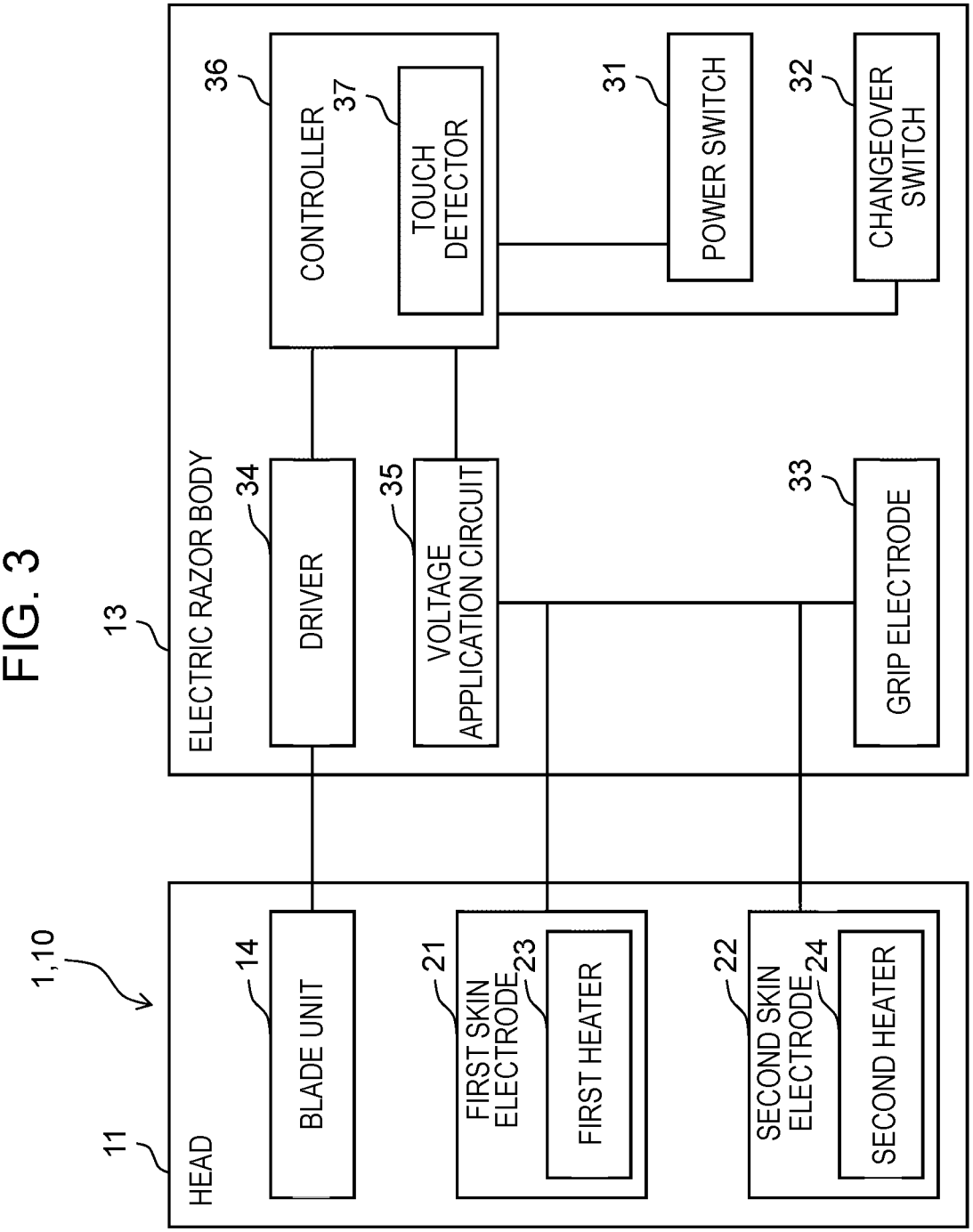
FIG. 3 is a block diagram illustrating a functional configuration of the electric razor according to the exemplary embodiment.

Driver (motor) 34, voltage application circuit 35, controller 36, and the like are housed in electric razor body 13 (see FIG. 3).

Next, a functional configuration of electric razor 10 will be described with reference to FIG. 3.

As illustrated in FIG. 3, electric razor 10 includes driver 34 for driving blade unit 14, and voltage application circuit 35 for applying voltages to first skin electrode 21, second skin electrode 22, and grip electrode 33.

Electric razor 10 includes controller 36. Controller 36 receives signals from power switch 31 and changeover switch 32, and controls driver 34, voltage application circuit 35, and the like according to the signals.

Controller 36 also includes touch detector 37 that detects the touch of the skin surface of the user with first skin electrode 21. As will be described in detail later, touch detector 37 has a function of detecting whether or not first skin electrode 21 sufficiently touches the skin surface of the user.

Controller 36 controls voltage application circuit 35 to change a frequency of the voltage (pulse) which is applied to at least first skin electrode 21 on the basis of the detection result of touch detector 37.

[2. Operation]

Next, operations and effects of electric razor 10 according to the present exemplary embodiment will be described.

Controller 36 has a plurality of modes as the skin care modes. In the present exemplary embodiment, controller 36 has three skin care modes of an ion introduction mode, an electroporation mode, and a microcurrent mode.

Figure 4:
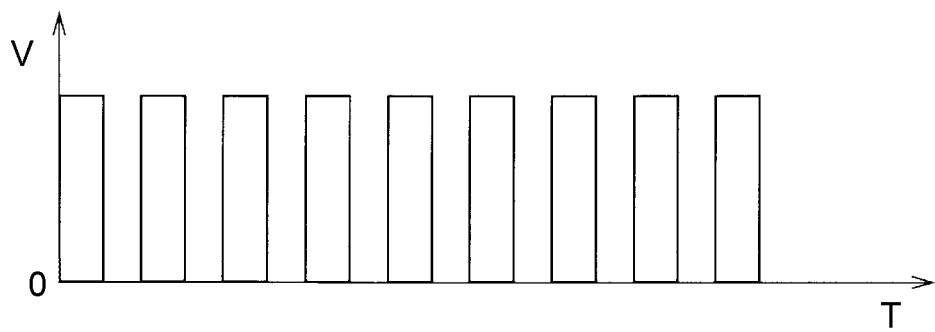
FIG. 4 is a waveform chart illustrating an example of a voltage (pulses) to be applied by a voltage application circuit in an ion introduction mode.

First, FIG. 4 illustrates a waveform chart of a voltage (pulse) which is applied between first skin electrode 21 and grip electrode 33 in the ion introduction mode. In FIG. 4, a vertical axis represents voltage V, and a horizontal axis represents time T.

In the ion introduction mode, controller 36 controls voltage application circuit 35 to energize a DC current between first skin electrode 21 and grip electrode 33.

In the ion introduction mode, a DC current in a direction in which first skin electrode 21 is an anode (positive electrode) and grip electrode 33 is a cathode (negative electrode) is applied to first skin electrode 21 and grip electrode 33.

In the ion introduction mode, for example, voltage V is greater than 0 V and less than or equal to 45 V, a frequency of voltage V (pulse) is between 1 kHz and 5 kHz, and a duty ratio of voltage V (pulse) is between 10% and 90%.

In the ion introduction mode, the user selects the ion introduction mode by using changeover switch 32. The user applies a lotion containing a moisture keeping component and a skin care agent such as a pre-shave lotion to a shaving part (for example, the face of the user), and then shaves hair by using electric razor 10.

In the ion introduction mode, voltage V for ion introduction is applied between first skin electrode 21 and grip electrode 33. As a result, the current flows from first skin electrode 21 to the shaving part, from the shaving part to an arm of the user carrying electric razor 10 through the stratum corneum, and from the arm to grip electrode 33. Thus, the moisture keeping component contained in the skin care agent efficiently permeates the shaving part, and thus, the skin quality of the user is improved.

The shaving part is warmed by warming first skin electrode 21 to a predetermined temperature by using first heater 23, and the moisture keeping component contained in the skin care agent efficiently permeates from the shaving part by a temperature effect (warming effect).

Hereinafter, the detection of the touch by touch detector 37 and switching between the frequencies of the voltage (pulse) on the basis of the detection result of touch detector 37 will be described with reference to FIG. 5.

Figure 5:
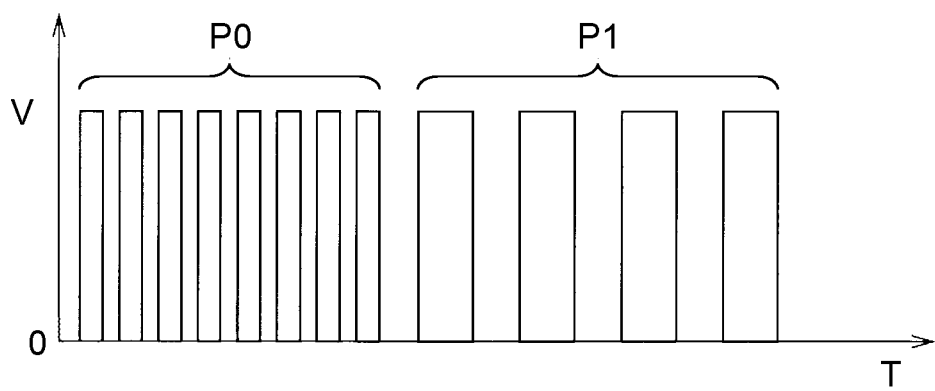
FIG. 5 is a waveform chart illustrating an example of a voltage (pulses) to be applied by the voltage application circuit before and after detection of the touch by a touch detector.

FIG. 5 illustrates a waveform chart of voltages (pulses) which is applied between first skin electrode 21 and grip electrode 33 before and after the touch detection by touch detector 37. Also in FIG. 5, a vertical axis represents voltage V, and a horizontal axis represents time T.

In the ion introduction mode, first, before first skin electrode 21 sufficiently touches the shaving part, a first voltage (touch detection pulse P0) having a relatively high frequency for touch detection is applied between first skin electrode 21 and grip electrode 33. Since the frequency of the first voltage (touch detection pulse P0) is a relatively high frequency, the user is less likely to feel electrical pain caused due to energization when first skin electrode 21 touches the skin surface of the user.

On the other hand, a touch resistance value is detected from a current value flowing between first skin electrode 21 and grip electrode 33, and whether or not first skin electrode 21 sufficiently touches the skin surface of the user is determined on the basis of the touch resistance value. For example, when the detected touch resistance value matches a predetermined touch resistance value, touch detector 37 determines that first skin electrode 21 sufficiently touches the skin surface of the user.

When it is determined that first skin electrode 21 sufficiently touches the skin surface of the user, a second voltage (ion introduction pulse P1) having a frequency lower than the first voltage (touch detection pulse P0) is applied between first skin electrode 21 and grip electrode 33. Since the frequency of the second voltage (ion introduction pulse P1) is a relatively low frequency, the ion introduction effect on the skin surface of the user is high.

When ion introduction pulse P1 is output, for example, voltage V is larger than 0 V and less than or equal to 45 V, the frequency of voltage V (pulse) is between 1 kHz and 5 kHz, and the duty ratio of voltage V (pulse) is between 10% and 90%.

In the case of constant voltage control, a touch detection method by touch detector 37 may be performed such that a current value flowing between first skin electrode 21 and grip electrode 33 is detected and whether or not first skin electrode 21 sufficiently touches the skin surface of the user may be determined on the basis of the current value. For example, when the detected current value is equal to or larger than a predetermined current value (threshold value), touch detector 37 determines that first skin electrode 21 sufficiently touches the skin surface of the user.

When the frequencies of the voltage which is applied are switched, controller 36 may control voltage application circuit 35 to gradually decrease the frequency of voltage V from the first voltage (touch detection pulse P0) to the second voltage (ion introduction pulse P1) in a stepwise manner.

In order to more reliably reduce the pain felt by the user, touch detector 37 may, for example, count the number of pulses of the current value equal to or greater than the threshold value, and then may determine that first skin electrode 21 sufficiently touches the skin surface of the user. That is, touch detector 37 may determine that first skin electrode 21 sufficiently touches the skin surface of the user after a predetermined time (corresponding to the number of counted pulses) elapses from the detection of the current value equal to or greater than the threshold value.

Figure 6:
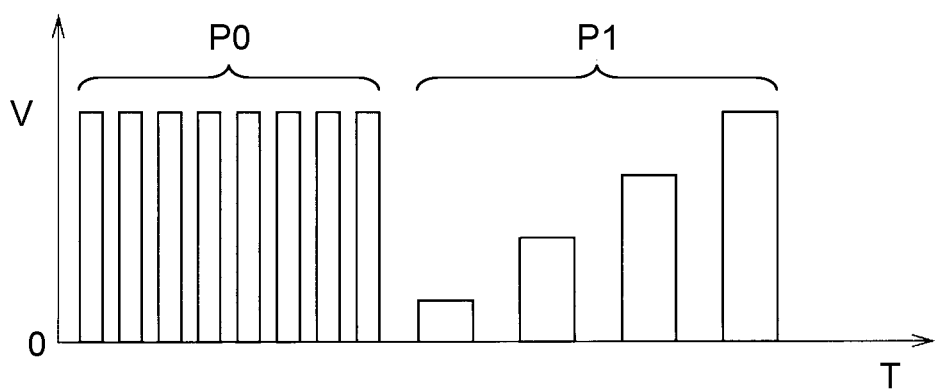
FIG. 6 is a waveform chart illustrating another example of the voltage (pulses) to be applied by the voltage application circuit before and after the detection of the touch by the touch detector.

In order to further reliably reduce the pain felt by the user, as illustrated in FIG. 6, controller 36 may control voltage application circuit 35 to gradually increase the magnitude of the value of voltage V which is applied between first skin electrode 21 and grip electrode 33 in a stepwise manner.

Figure 7:
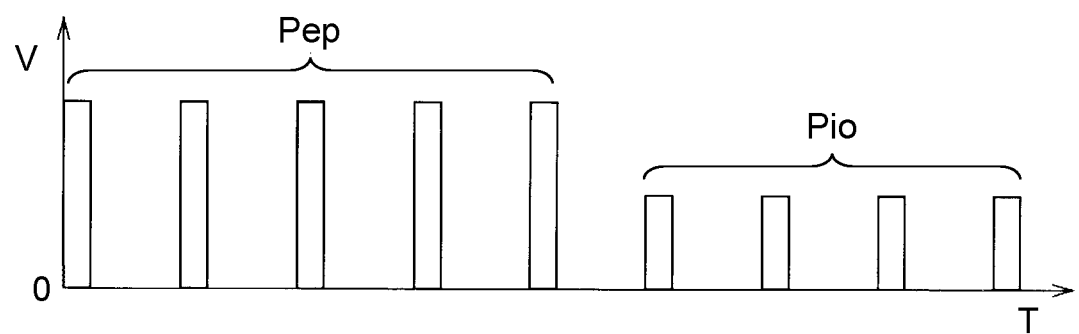
FIG. 7 is a waveform chart illustrating an example of a voltage (pulses) to be applied by the voltage application circuit in an electroporation mode.

Next, FIG. 7 illustrates a waveform chart of voltages (pulses) which is applied between second skin electrode 22 and grip electrode 33 or first skin electrode 21, or between first skin electrode 21 and grip electrode 33 in the electroporation mode. Also in FIG. 7, a vertical axis represents voltage V, and a horizontal axis represents time T.

In the electroporation mode, controller 36 controls voltage application circuit 35 to perform energization of electroporation (electric punch method) between second skin electrode 22 and grip electrode 33 or first skin electrode 21.

On the basis of an output of electroporation pulse Pep (see FIG. 7), a DC current in a direction in which second skin electrode 22 is an anode (positive electrode) and grip electrode 33 is a cathode (negative electrode) is applied to second skin electrode 22 and grip electrode 33.

Alternatively, on the basis of the output of electroporation pulse Pep, a DC current in a direction in which second skin electrode 22 is an anode (positive electrode) and first skin electrode 21 is a cathode (negative electrode) is applied to second skin electrode 22 and first skin electrode 21.

When electroporation pulse Pep is output, for example, voltage V is larger than 0 V and less than or equal to 80 V, the frequency of voltage V (pulse) is between 1 kHz and 5 kHz, and the duty ratio of voltage V (pulse) is between 1% and 90%.

On the basis of an output of ion introduction pulse Pio (see FIG. 7), a DC current in a direction in which first skin electrode 21 is an anode (positive electrode) and grip electrode 33 is a cathode (negative electrode) is applied to first skin electrode 21 and grip electrode 33.

When ion introduction pulse Pio is output, for example, voltage V is larger than 0 V and less than or equal to 45 V, the frequency of voltage V (pulse) is between 1 kHz and 5 kHz, and the duty ratio of voltage V (pulse) is between 10% and 90%.

In the electroporation mode, the user selects the electroporation mode by using changeover switch 32. Similarly to the case of the ion introduction mode, the user applies the skin care agent containing the moisture keeping component to the shaving part, and then shaves the hair by using electric razor 10.

First, a voltage of a relatively high voltage (electroporation pulse Pep) is applied between second skin electrode 22 and grip electrode 33 or first skin electrode 21, and an electroporation current flows through the shaving part therebetween. Thus, a lamellar structure of the stratum corneum in the shaving part between second skin electrode 22 and grip electrode 33 or first skin electrode 21 is loosened, and the moisture keeping component of the polymer contained in the skin care agent easily permeates the shaving part.

The voltage for ion introduction (ion introduction pulse Pio) is immediately applied between first skin electrode 21 and grip electrode 33. As a result, the current flows from first skin electrode 21 to the shaving part, from the shaving part to an arm of the user carrying electric razor 10 through the stratum corneum, and from the arm to grip electrode 33. Thus, the moisture keeping component contained in the skin care agent efficiently permeates the shaving part, and thus, the skin quality of the user is improved.

The shaving part is warmed by warming first skin electrode 21 and second skin electrode 22 to a predetermined temperature by using heaters 23 and 24, respectively, and the moisture keeping component contained in the skin care agent efficiently permeates from the shaving part by the temperature effect (heating effect).

Similarly to the case of the ion introduction mode, the detection of the touch by touch detector 37 and the switching between the frequencies of voltage V (pulse) on the basis of the detection result of touch detector 37 described above can also be performed in the electroporation mode.

Figure 8:
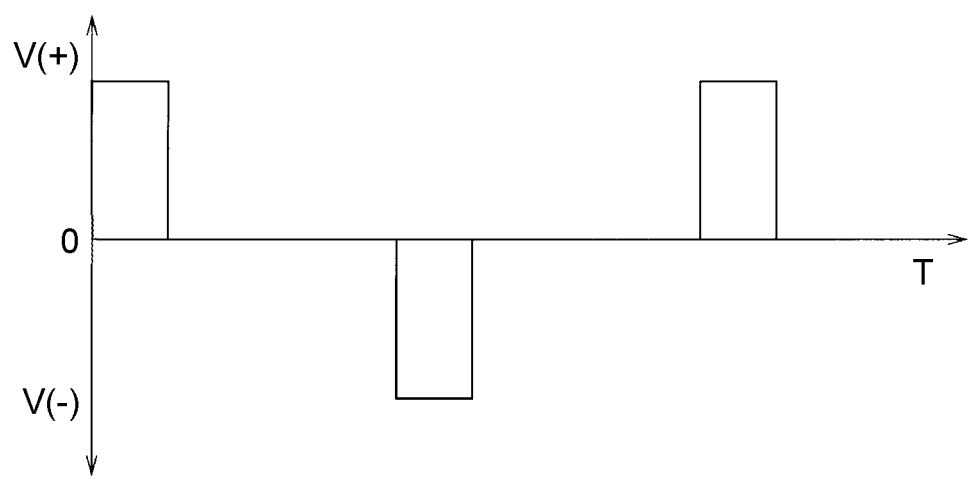
FIG. 8 is a waveform chart illustrating an example of a voltage (pulses) to be applied by the voltage application circuit in a micro-current mode.

Next, FIG. 8 illustrates a waveform chart of a voltage (pulse) which is applied between first skin electrode 21 and grip electrode 33 in the microcurrent mode. In FIG. 8, a vertical axis represents voltage V, and a horizontal axis represents time T.

In the microcurrent mode, controller 36 controls voltage application circuit 35 to energize microcurrent (weak current) between first skin electrode 21 and grip electrode 33.

In the microcurrent mode, an AC current is applied between first skin electrode 21 and grip electrode 33.

In the microcurrent mode, for example, voltage V is greater than 0 V and less than or equal to 45 V, the frequency of voltage V (pulse) is between 1 kHz and 5 kHz, and the duty ratio of voltage V (pulse) is between 10% and 90%.

For example, when the skin care agent is not used, the user can select the microcurrent mode. In the microcurrent mode, the user selects the microcurrent mode by using changeover switch 32, and shaves hair by using electric razor 10.

In the microcurrent mode, a voltage of a relatively low voltage is applied between first skin electrode 21 and grip electrode 33. As a result, the current alternately flows from first skin electrode 21 to the shaving part, from the shaving part to the arm of the user having electric razor 10 through the stratum corneum, and from the arm to grip electrode 33. Thus, the skin quality of the user is improved by activating the skin surface of the shaving part.

Similarly to the case of the ion introduction mode, the detection of the touch by touch detector 37 and the switching between the frequencies of the voltage (pulse) on the basis of the detection result of touch detector 37 described above can also be performed in the microcurrent mode.

[3. Effects and the Like]

(1) In the present exemplary embodiment, beauty instrument 1 includes head 11 and grip 12. Beauty instrument 1 includes skin electrode (first skin electrode) 21 disposed at the position of head 11 where the skin electrode touches the skin surface of the human body, and grip electrode 33 disposed at the position of grip 12 where the grip touches the finger of the human body. Beauty instrument 1 includes voltage application circuit 35 for applying the voltage between first skin electrode 21 and grip electrode 33 to cause the current to flow between first skin electrode 21 and grip electrode 33 through the human body, and controller 36 that controls voltage application circuit 35. Controller 36 includes touch detector 37 that detects the touch of the skin surface of the human body with first skin electrode 21, and controls voltage application circuit 35 to apply the first voltage when touch detector 37 does not detect the touch. When touch detector 37 detects the touch, controller 36 controls voltage application circuit 35 to apply the second voltage having the frequency lower than the frequency of the first voltage.

Beauty instrument 1 includes touch detector 37 that detects whether or not first skin electrode 21 sufficiently touches the skin surface of the user, and thus, it is possible to suppress generation of an inrush current that may be generated when first skin electrode 21 does not sufficiently touch the skin surface. Therefore, the electrical pain on the skin surface of the user can be reduced during the use of beauty instrument 1. As the voltage which is applied between first skin electrode 21 and grip electrode 33 has a higher frequency, the electrical pain felt by the user can be further reduced.

(2) As in the present exemplary embodiment, touch detector 37 may detect the touch of the skin surface of the human body with first skin electrode 21 on the basis of the magnitude of the value of the current flowing between first skin electrode 21 and grip electrode 33 during the constant voltage control.

As a result, it is possible to accurately determine that first skin electrode 21 sufficiently touches the skin surface of the user.

(3) Touch detector 37 may detect the touch of the skin surface of the human body with first skin electrode 21 on the basis of the number of pulses of the current flowing between first skin electrode 21 and grip electrode 33 during the constant voltage control.

As a result, it is possible to more accurately determine that first skin electrode 21 sufficiently touches the skin surface of the user.

(4) Touch detector 37 may control voltage application circuit 35 to gradually decrease the frequency of the voltage from the first voltage to the second voltage after touch detector 37 detects the touch.

As a result, the pain felt by the user can be more reliably reduced, and the skin care treatment can be appropriately performed.

(5) Touch detector 37 may control voltage application circuit 35 to gradually increase the magnitude (potential) of the value of the voltage which is applied between first skin electrode 21 and grip electrode 33 after touch detector 37 detects the touch.

As a result, the pain felt by the user can be more reliably reduced, and the skin care treatment can be more appropriately performed.

(6) In the present exemplary embodiment, electric razor 10 includes head 11, grip 12, and blade unit 14 that is disposed on head 11 for cutting hair. Electric razor 10 also includes first skin electrode 21 disposed at the position of head 11 touching the skin surface of the human body during cutting of hair, and grip electrode 33 disposed at the position of grip 12 touching the finger of the human body during cutting of hair. Electric razor 10 further includes voltage application circuit 35 for applying the voltage between first skin electrode 21 and grip electrode 33 to cause the current to flow between first skin electrode 21 and grip electrode 33 through the human body, and controller 36 that controls voltage application circuit 35. Controller 36 includes touch detector 37 that detects the touch of the skin surface of the human body with first skin electrode 21, and controls voltage application circuit 35 to apply the first voltage when touch detector 37 does not detect the touch. When touch detector 37 detects the touch, controller 36 controls voltage application circuit 35 to apply the second voltage having the frequency lower than the frequency of the first voltage.

Electric razor 10 includes touch detector 37 that detects whether or not first skin electrode 21 sufficiently touches the skin surface of the user, and thus, the generation of the inrush current that may be generated when first skin electrode 21 does not sufficiently touch the skin surface can be suppressed. Accordingly, the electrical pain on the skin surface of the user can be reduced during the use of electric razor 10. As the voltage which is applied between first skin electrode 21 and grip electrode 33 has a higher frequency, the electrical pain felt by the user can be further reduced.

Note that, controller 36 and touch detector 37 include, for example, a microcontroller having one or more processors and one or more memories. The microcontroller achieves a function as controller 36 and touch detector 37 by executing a program recorded in one or more memories by one or more processors. The program may be recorded in a memory in advance, may be provided by being recorded in a non-transitory recording medium such as a memory card, or may be provided through an electric communication line. In other words, the program is a program for causing one or more processors to function as controller 36 and touch detector 37.

Note that, the above exemplary embodiment is to exemplify the techniques in the present disclosure, and therefore, various modifications, replacements, additions, omissions, and the like can be made in the scope of the appended claims or in an equivalent scope thereof.

The present disclosure is applicable to a beauty instrument and an electric razor that can prevent a user from feeling pain when an electrode touches a skin surface of the user during treatment or cutting of hair. Specifically, the present disclosure is applicable to beauty instruments such as a facial treatment device and a face massage device in addition to the electric razor.

REFERENCE MARKS IN THE DRAWINGS 1, 1A, 1B: beauty instrument
10, 10A, 10B: electric razor
11: head
12: grip
13: electric razor body
14: blade unit
15: outer net blade (first outer net blade)
16: outer slit blade
17: outer net blade (second outer net blade)
21: skin electrode (first skin electrode)
22: skin electrode (second skin electrode)
23: heater (first heater)
24: heater (second heater)
31: power switch
32: changeover switch
33: grip electrode
34: driver (motor)
35: voltage application circuit
36: controller (controller)
37: touch detector

The invention claimed is:

1. A beauty instrument comprising:
a head;
a grip;
a skin electrode that is disposed at a position of the head touching a skin surface of a human body;
a grip electrode that is disposed at a position of the grip touching a finger of the human body;
a voltage application circuit for applying a voltage between the skin electrode and the grip electrode to cause a current to flow between the skin electrode and the grip electrode through the human body; and
a controller that controls the voltage application circuit, wherein
the controller
comprises a touch detector that detects touch of the skin surface of the human body with the skin electrode,
controls the voltage application circuit to apply a first voltage when the touch detector does not detect the touch, and
controls the voltage application circuit to apply a second voltage having a frequency lower than a frequency of the first voltage when the touch detector detects the touch.

2. The beauty instrument according to claim 1, wherein the touch detector detects the touch of the skin surface of the human body with the skin electrode on the basis of a magnitude of a value of the current flowing between the skin electrode and the grip electrode during constant voltage control.

3. The beauty instrument according to claim 1, wherein the touch detector detects the touch of the skin surface of the human body with the skin electrode on the basis of a number of pulses of the current flowing between the skin electrode and the grip electrode during constant voltage control.

4. The beauty instrument according to claim 1,
wherein the controller controls the voltage application circuit to gradually decrease a frequency of the voltage from the first voltage to the second voltage after the touch detector detects the touch.

5. The beauty instrument according to claim 1, wherein the controller controls the voltage application circuit to gradually increase a magnitude of a value of the voltage which is applied between the skin electrode and the grip electrode after the touch detector detects the touch.

6. An electric razor comprising:
a head;
a grip;
a blade unit that is disposed in the head for cutting hair;
a skin electrode that is disposed at a position of the head touching a skin surface of a human body during cutting of hair;
a grip electrode that is disposed at a position of the grip touching a finger of the human body during the cutting of hair;
a voltage application circuit for applying a voltage between the skin electrode and the grip electrode to cause a current to flow between the skin electrode and the grip electrode through the human body; and
a controller that controls the voltage application circuit, wherein
the controller
comprises a touch detector that detects touch of the skin surface of the human body with the skin electrode,
controls the voltage application circuit to apply a first voltage when the touch detector does not detect the touch, and
controls the voltage application circuit to apply a second voltage having a frequency lower than a frequency of the first voltage when the touch detector detects the touch.

7. The electric razor according to claim 6, wherein
the touch detector detects the touch of the skin surface of the human body with the skin electrode on the basis of a magnitude of a value of the current flowing between the skin electrode and the grip electrode during constant voltage control.

8. The electric razor according to claim 6, wherein
the touch detector detects the touch of the skin surface of the human body with the skin electrode on the basis of a number of pulses of the current flowing between the skin electrode and the grip electrode during constant voltage control.

9. The electric razor according to claim 6, wherein
the controller controls the voltage application circuit to gradually decrease a frequency of the voltage from the first voltage to the second voltage after the touch detector detects the touch.

10. The electric razor according to claim 6, wherein
the controller controls the voltage application circuit to gradually increase a magnitude of a value of the voltage which is applied between the skin electrode and the grip electrode after the touch detector detects the touch.

\* \* \* \* \*